United States Patent
Askins et al.

(10) Patent No.: US 8,309,363 B2
(45) Date of Patent: Nov. 13, 2012

(54) APPARATUS AND METHOD FOR EVALUATING A HYDROCARBON TO DETERMINE THE PROPENSITY FOR COKE FORMATION

(75) Inventors: John S Askins, Derby (GB); Timothy A Shepherd, Bargate (GB)

(73) Assignee: Rolls-Royce PLC, London (GB)

( * ) Notice: Subject to any disclaimer, the term of this patent is extended or adjusted under 35 U.S.C. 154(b) by 287 days.

(21) Appl. No.: 12/453,429

(22) Filed: May 11, 2009

(65) Prior Publication Data
US 2009/0305428 A1 Dec. 10, 2009

(30) Foreign Application Priority Data
Jun. 6, 2008 (GB) .................................. 0810299.8

(51) Int. Cl.
*G01N 33/26* (2006.01)
*C10L 5/40* (2006.01)
*C10G 9/20* (2006.01)

(52) U.S. Cl. ............ 436/139; 436/145; 422/78; 44/607; 208/132

(58) Field of Classification Search .......... None
See application file for complete search history.

(56) References Cited

U.S. PATENT DOCUMENTS

| | | | | |
|---|---|---|---|---|
| 1,940,955 A * | 12/1933 | Laird | ............................ | 208/106 |
| 1,983,386 A * | 12/1934 | Mikeska | ........................ | 122/23 |
| 3,248,927 A * | 5/1966 | Buehler et al. | .................. | 374/45 |
| 4,127,473 A * | 11/1978 | Hozuma et al. | ............... | 208/130 |
| 4,726,934 A * | 2/1988 | Yates et al. | .................... | 422/150 |
| 4,985,136 A * | 1/1991 | Bartholic | ....................... | 208/153 |
| 2003/0201334 A1* | 10/2003 | Wells et al. | .................... | 239/11 |
| 2004/0065590 A1* | 4/2004 | Chan et al. | .................... | 208/146 |
| 2007/0045098 A1* | 3/2007 | Gawad | ......................... | 202/245 |

FOREIGN PATENT DOCUMENTS
FR 2 880 689 A1 7/2006

* cited by examiner

*Primary Examiner* — Yelena G Gakh
*Assistant Examiner* — Michelle Adams
*(74) Attorney, Agent, or Firm* — Oliff & Berridge, PLC

(57) ABSTRACT

An apparatus (10) for evaluating a liquid hydrocarbon to determine the propensity for coke formation comprising an injector (12), a supply of air (14) arranged to supply air to the injector (12) and a supply of liquid hydrocarbon (16) arranged to supply liquid hydrocarbon to the injector (12). The injector (12) is arranged to atomise the liquid hydrocarbon and to supply the air and atomised liquid hydrocarbon into a chamber (18) and the chamber (18) is arranged to supply atomised liquid hydrocarbon and air to a test pipe (20) and a heater (22) is arranged to heat the test pipe (20). The test pipe (20) is pivotably mounted on a frame (28) such that the orientation of the test pipe (20) relative to the frame (28) is variable. The apparatus (10) is able to simulate conditions within a vent pipe of a lubricant system of an aero gas turbine engine.

28 Claims, 3 Drawing Sheets

APPARATUS AND METHOD FOR EVALUATING A HYDROCARBON TO DETERMINE THE PROPENSITY FOR COKE FORMATION

BACKGROUND

The present invention relates to an apparatus for evaluating a liquid hydrocarbon to determine the propensity for coke formation and in particular to an apparatus for evaluating lubricant, or oil, to determine the propensity for coke formation.

In a prior art apparatus for evaluating a lubricant or oil, to determine the propensity for coke formation, the apparatus comprises a supply of oil, lubricant, in a reservoir and a heater to heat the oil in the reservoir. A supply of air is arranged to supply air into the oil in the reservoir such that the air is bubbled through the oil. The reservoir is arranged to supply the air to a vertical test pipe and a heater is provided to heat the test pipe. A thermocouple is arranged to measure the temperature of the oil in the reservoir. The mass, weight, of the deposit on the test pipe is used to give a measure of the propensity for coke formation.

However, the air flow through the test pipe contains a fraction of oil vapour and forms deposits, coke, on the test pipe. Thus, a first problem with this apparatus is that the evaluation only determines the propensity for coke formation for a fraction of the oil and not the fully formulated oil. A second problem with this apparatus is that the evaluation only determines the propensity for coke formation for a vertical test pipe.

SUMMARY

Accordingly the present invention seeks to provide a novel apparatus for evaluating a liquid hydrocarbon to determine the propensity for coke formation which reduces, preferably overcomes, the above mentioned problem.

Accordingly the present invention provides an apparatus for evaluating a liquid hydrocarbon to determine the propensity for coke formation comprising an injector, a supply of air arranged to supply air to the injector, a supply of liquid hydrocarbon arranged to supply liquid hydrocarbon to the injector. The injector is arranged to atomise the liquid hydrocarbon and to supply the air and atomised liquid hydrocarbon into a chamber, the chamber is arranged to supply atomised liquid hydrocarbon and air to a test pipe and a heater to heat the test pipe.

Preferably the chamber is arranged to return liquid hydrocarbon to the supply of hydrocarbon.

Preferably the supply of liquid hydrocarbon is arranged to supply the liquid hydrocarbon to the injector via a pump.

Preferably the supply of liquid hydrocarbon is a reservoir.

Preferably the test pipe is mounted on a frame.

Preferably the test pipe is variably mounted on the frame such that the orientation of the test pipe relative to the frame is variable. Preferably the test pipe is pivotably mounted on the frame.

Preferably the heater comprises a heating block arranged around the test pipe.

Preferably the supply of liquid hydrocarbon comprises a supply of lubricant or oil.

The present invention also provides a method of evaluating a liquid hydrocarbon to determine the propensity for coke formation the method comprising supplying air to an injector, supplying liquid hydrocarbon to the injector, atomising the liquid hydrocarbon, supplying air and atomised liquid hydrocarbon from the injector into a chamber, supplying atomised liquid hydrocarbon and air to a test pipe, heating the test pipe to produce coking deposition in the test pipe and measuring the mass of coking deposited in the test pipe.

Preferably the method comprises supplying lubricant or oil to the injector.

Preferably, the method comprises mounting the test pipe on a frame such that the test pipe is variably mounted on the frame. The orientation of the test pipe is varied relative to the frame and the propensity for coke formation is determined at different orientations of the test pipe.

BRIEF DESCRIPTION OF THE DRAWINGS

The present invention will be more fully described by way of example with reference to the accompanying drawings in which.

DETAILED DESCRIPTION OF EMBODIMENTS

Figure 1:
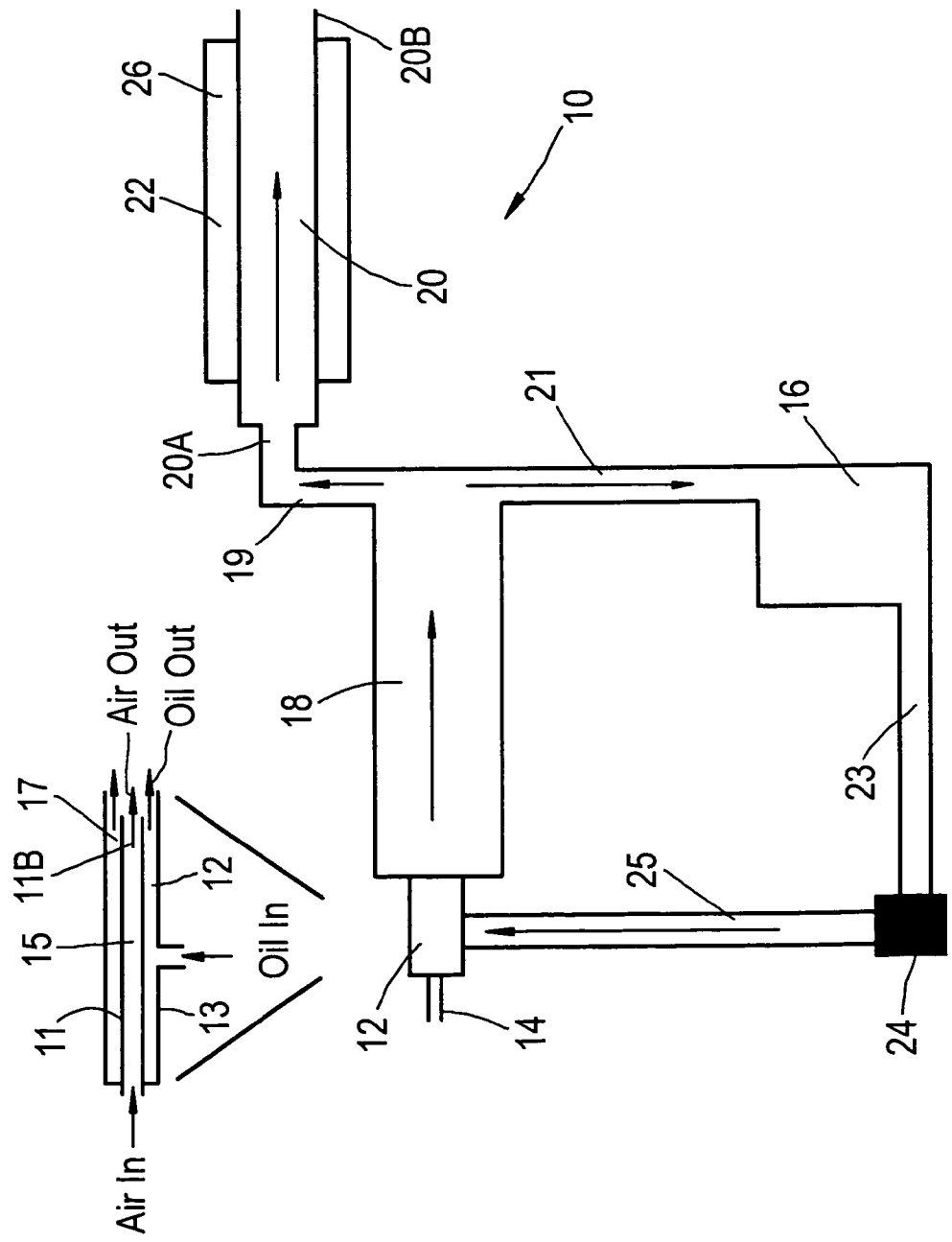
FIG. 1 shows a schematic view of an apparatus for evaluating a lubricant to determine the propensity for coke formation according to the present disclosure.

An apparatus 10 for evaluating a lubricant (oil) to determine the propensity for coke formation is shown in FIG. 1 and the apparatus 10 comprises an injector 12, a supply of air 14, a supply of lubricant e.g. oil, 16, a chamber 18 and a test pipe 20. The supply of air 14 is arranged to supply air to the injector 12 and the supply of lubricant (oil) 16 is arranged to supply lubricant (oil) to the injector 12. The injector 12 is arranged to atomise the lubricant (oil) and supply the air and atomised lubricant (oil) into a chamber 18. The chamber 18 is arranged to supply atomised lubricant (oil) and air to the test pipe 20 via a conduit 19 and the heater 22 is arranged around the test pipe 20 to heat the test pipe 20 and thus heat the atomised lubricant (oil) in the test pipe 20. The chamber 18 is arranged to return and supply, liquid, un-atomised, lubricant (oil) back to the supply of lubricant (oil) 16 via a conduit 21. The supply of lubricant (oil) 16 is arranged to supply the lubricant (oil) to the injector 12 via a conduit 23, a pump 24 and a conduit 25. The supply of lubricant (oil) 16 is actually a reservoir. The heater 22 comprises a heating block 26 arranged around the test pipe 20 and for example comprises a brass heating block.

The injector 12 comprises an inner cylindrical member 11 and a coaxial outer cylindrical member 13. An inner flow path 15 for air is defined by the inner cylindrical member 11. A coaxial outer annular flow path 17 for lubricant (oil) is defined between the inner cylindrical member 11 and the outer cylindrical member 13.

In operation air and lubricant (oil) are supplied to the injector 12 and the injector atomises some of the lubricant (oil) to form a lubricant mist, an oil mist, in the air even at ambient temperatures. The lubricant (oil) is atomised by the shearing force of the air expanding out of the injector 12 into the chamber 18. The lubricant flows along the outer annular flow path 17 between the inner and outer cylindrical members 11 and 13 and the air flows along the inner flow path 15 within the inner cylindrical member 11. The lubricant (oil) is atomised at the downstream end 11B of the inner cylindrical member 11. The lubricant (oil) is atomised due to the air expanding out of the inner cylindrical member 11 and producing shearing of the lubricant (oil) immediately around the air. The shearing action breaks the lubricant (oil) into small droplets, atomises the lubricant (oil). The atomised lubricant (oil) e.g. the lubricant (oil) droplets, is carried by the flow of air through the chamber 18 and the conduit 19 to the test pipe 20. Any un-atomised lubricant (oil) is returned by the conduit 21 to the supply of lubricant (oil) 16. The atomised lubricant (oil) in the air or the lubricant (oil) mist flows through the test pipe 20, which is heated by the heater 22. The heating block 26 produces high wall temperatures in the test pipe 20. The lubricant (oil) collects and wets out, on the inner surface of the test pipe 20 and the lubricant (oil) on the inner surface of the test pipe 20 is subjected to high temperatures, which results in the degradation of the lubricant (oil) and the formation of carbonaceous deposits, e.g. coke or coking.

FIGS. 2 to 5 show the test pipe 20 of the apparatus 10 of FIG. 1 mounted on a frame 28. The test pipe 20 is variably mounted on the frame 28 such that the orientation of the test pipe 20 relative to the frame 28 is variable. In particular the test pipe 20 is pivotably mounted on the frame 28 by a pivot 30 and the test pipe 20 is then locked in the selected orientation by a lock 32. Thus the present invention mounts the test pipe 20 on a frame 28 such that the test pipe 20 is variably mounted on the frame 28, then the orientation of the test pipe 20 relative to the frame 28 is varied and the propensity for coke formation at different orientations of the test pipe 20 is determined.

Figure 2:
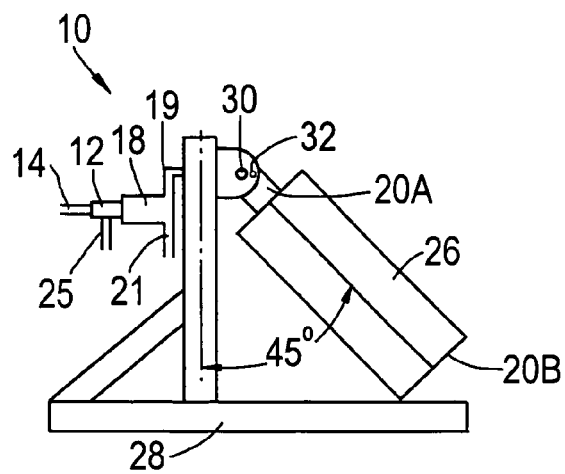
FIG. 2 shows the apparatus shown in FIG. 1 and a frame and the test pipe in a first orientation.

FIG. 2 shows the test pipe 20 arranged at an angle of 45° to the vertical direction and such that the outlet 20B of the test pipe 20 is arranged at a lesser height, lower down than, the inlet 20A.

Figure 3:
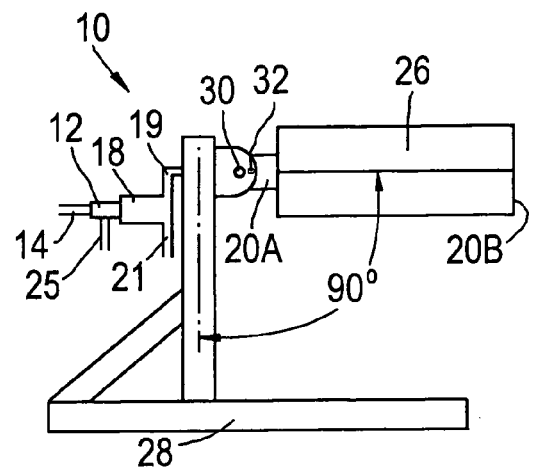
FIG. 3 shows the apparatus shown in FIG. 1 and a frame and the test pipe in a second orientation.

FIG. 3 shows the test pipe 20 arranged at an angle of 90° to the vertical direction, e.g. horizontal, and such that the outlet 20B of the test pipe 20 is arranged at the same height as the inlet 20A.

Figure 4:
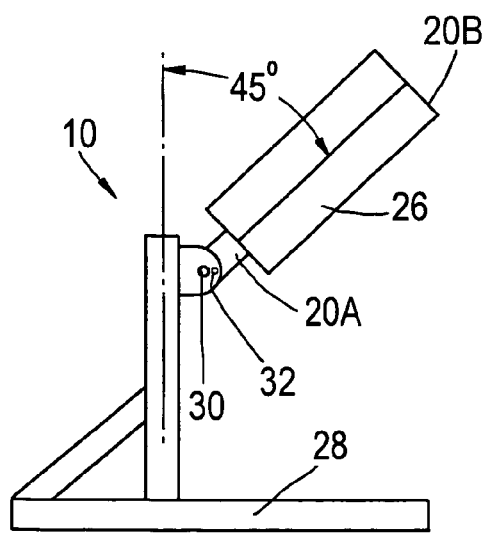
FIG. 4 shows the apparatus shown in FIG. 1 and a frame and the test pipe in a third orientation.

FIG. 4 shows the test pipe 20 arranged at an angle of 45° to the vertical direction and such that the outlet 20B of the test pipe 20 is arranged at a greater height, higher up than, the inlet 20A.

Figure 5:
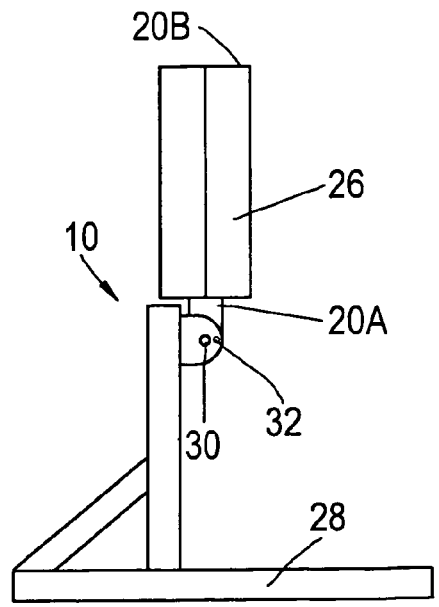
FIG. 5 shows the apparatus shown in FIG. 1 and a frame and the test pipe in a fourth orientation.

FIG. 5 shows the test pipe 20 arranged parallel to the vertical direction, e.g. vertical, and such that the outlet 20B of the test pipe 20 is arranged at a greater height than the inlet 20A.

The apparatus for evaluating a lubricant (oil) to determine the propensity for coke formation according to the present invention is able to differentiate between standard oil STD and HPC oils. HPC oil is high performance capability oil and defined in SAE International Standard-Specification for Aero and Aero-Derived Gas Turbine Engine Lubricants. HPC oils produce less carbonaceous deposits, coking, than standard oils STD according to the apparatus.

Figure 6:
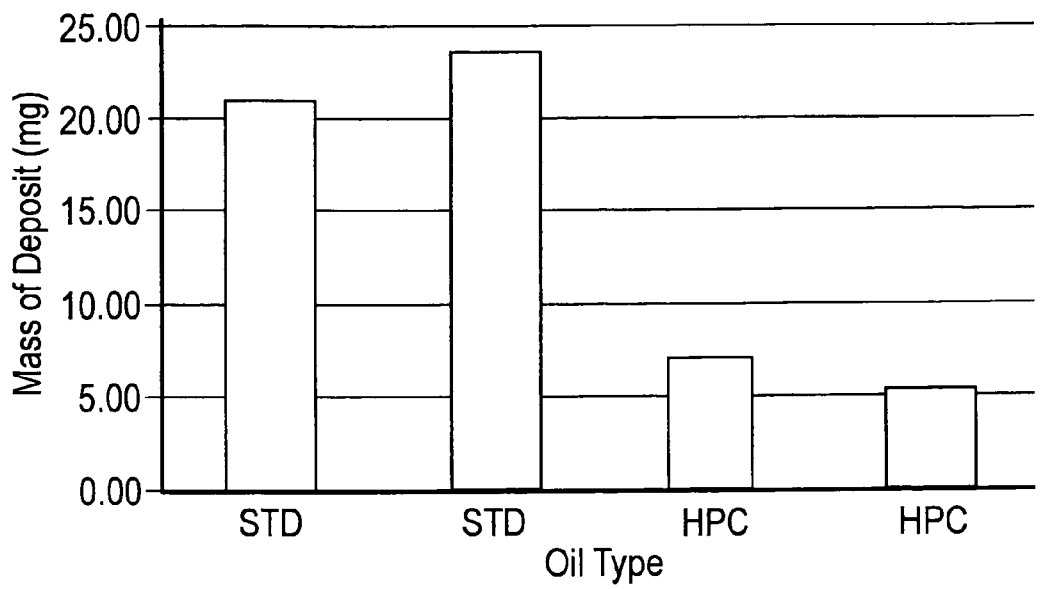
FIG. 6 is a graph of mass of deposit versus oil type.

FIG. 6 is a graph of mass of deposit versus oil type tested in the apparatus according to the present disclosure. The graph shows two tests for the standard oil STD and two tests for the HPC oil, and shows that the mass of deposit for HPC oils is less than that for standard oils STD. HPC oils produce less carbonaceous deposits, coking, than standard oils STD on aero gas turbine engine vent pipes, e.g. gas turbine engine lubricant system vent pipes.

The apparatus for evaluating a lubricant (oil) to determine the propensity for coke formation according to the present invention is able to differentiate between different orientations of the test pipe. A test pipe arranged vertically produces more carbonaceous deposits, coking, than a test pipe arranged at an angle below the horizontal, e.g. with the outlet of the test pipe at lesser height than the inlet of the test pipe.

Figure 7:
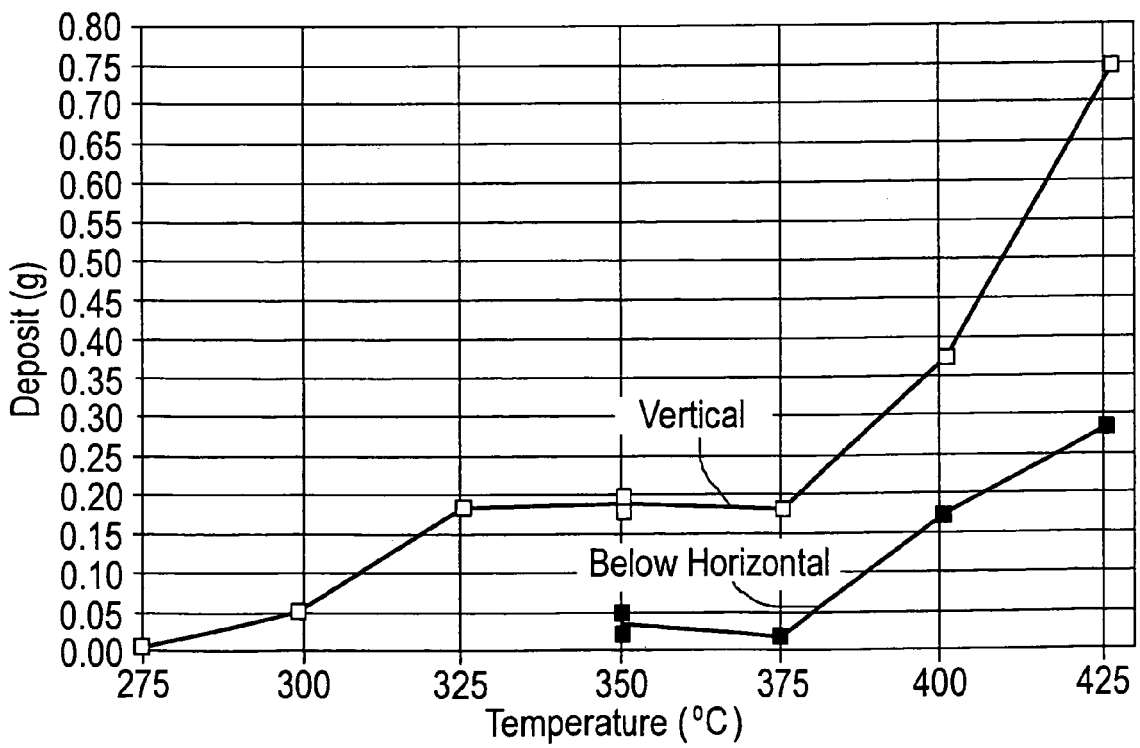
FIG. 7 is a graph of mass of deposit versus temperature for different orientations of the test pipe.

FIG. 7 is a graph of mass of deposit versus temperature for a vertical test pipe and a below horizontal test pipe for lubricant (oil) tested in the apparatus according to the present invention and it is seen that the mass of deposit for a vertical test pipe is greater than for a below horizontal test pipe. A vertical vent pipe on an aero gas turbine engine produces more deposition, coking, than a below horizontal vent pipe on an aero gas turbine engine.

The present invention is able to simulate a vent pipe of a lubricant system of an aero gas turbine engine and in particular the variable positioning of the test pipe is able to simulate different angles of vent pipe of a lubricant system on different aero gas turbine engines.

Although the present invention has been described with reference to evaluating a lubricant (oil) to determine the propensity for coke formation it may be equally possible to evaluate a liquid fuel, or liquid hydrocarbon, to determine the propensity for coke formation.

The invention claimed is:

1. An apparatus for evaluating a liquid hydrocarbon to determine propensity for coke formation, comprising:
   a chamber;
   an injector;
   an air supply that supplies air to the injector;
   a liquid hydrocarbon supply that supplies liquid hydrocarbon to the injector, the injector being arranged to atomise the liquid hydrocarbon and to supply the air and atomised liquid hydrocarbon into the chamber;
   a test pipe that is located outside the chamber;
   a first connecting portion that connects the chamber to the test pipe;
   a second connecting portion that connects the chamber to the liquid hydrocarbon supply;
   a third connecting portion that connects the liquid hydrocarbon supply to the injector; and
   a heater that heats the test pipe,
   wherein the chamber is arranged to supply the atomised liquid hydrocarbon and air through the first connecting portion to the test pipe and the heater.

2. The apparatus as claimed in claim 1, wherein the chamber is arranged to supply the liquid hydrocarbon to the liquid hydrocarbon supply.

3. The apparatus as claimed in claim 1, wherein the liquid hydrocarbon supply is arranged to supply the liquid hydrocarbon to the injector via a pump.

4. The apparatus as claimed in claim 1, wherein the liquid hydrocarbon supply is a reservoir.

5. The apparatus as claimed in claim 1, wherein the test pipe is mounted on a frame.

6. The apparatus as claimed in claim 5, wherein the test pipe is variably mounted on the frame such that the orientation of the test pipe relative to the frame is variable.

7. The apparatus as claimed in claim 6, the test pipe further comprising an inlet at a first end and an outlet at a second end that is opposite the first end, the first end being pivotally mounted on the frame.

8. The apparatus as claimed in claim 7, wherein a lock is provided to lock the test pipe in a selected orientation.

9. The apparatus as claimed in claim 7, wherein the test pipe has an inlet at a first end and an outlet at a second end that is opposite the first end such that the second end is movable such that the test pipe moves in a hinge-like motion.

10. The apparatus as claimed in claim 1, wherein the heater comprises a heating block arranged around the test pipe.

11. The apparatus as claimed in claim 1, wherein the liquid hydrocarbon supply comprises a supply of lubricant or oil.

12. The apparatus as claimed in claim 1, the first connecting portion having a first diameter and the chamber having a second diameter, the first diameter being different from the second diameter.

13. An apparatus for evaluating a liquid hydrocarbon to determine propensity for coke formation, comprising:
 a chamber;
 a test pipe that is located outside the chamber;
 a heater that heats the test pipe;
 an injector that is disposed on the chamber;
 an air supply that supplies air to the injector;
 a liquid hydrocarbon supply that supplies liquid hydrocarbon to the injector;
 a first connecting portion that connects the chamber to the test pipe:
 a second connecting portion that connects the chamber to the liquid hydrocarbon supply; and
 a third connecting portion that connects the liquid hydrocarbon supply to the injector, the injector being arranged to atomise the liquid hydrocarbon and to supply the air and atomised liquid hydrocarbon into the chamber, and the chamber being arranged to supply the atomised liquid hydrocarbon and air to the test pipe and the heater, wherein the injector includes:
  an inner cylindrical member that includes an inner flow path, and
  an outer cylindrical member that is coaxial with respect to the inner cylindrical member, an outer annular flow path being formed between the inner cylindrical member and the outer cylindrical member, the air supply supplies air to the inner flow path and the liquid hydrocarbon supply supplies the liquid hydrocarbon to the outer annular flow path.

14. An apparatus for evaluating a liquid hydrocarbon to determine propensity for coke formation comprising:
 a chamber;
 an injector;
 an air supply that supplies air to the injector;
 a liquid hydrocarbon supply that supplies the liquid hydrocarbon to the injector, the injector being arranged to atomise the liquid hydrocarbon and to supply the air and atomised liquid hydrocarbon into the chamber;
 a frame;
 a test pipe that has an inlet at a first end and an outlet at a second end that is opposite the first end, the first end being pivotally mounted on the frame; and
 a heater that heats the test pipe,
 wherein the chamber is arranged to supply the atomised liquid hydrocarbon and air to the test pipe and the heater, and the test pipe is pivotally mounted about a horizontal axis and the horizontal axis is arranged perpendicular with respect to a longitudinal direction of the test pipe, the longitudinal direction being a direction from the inlet at the first end to the outlet at the second end.

15. The apparatus as claimed in claim 14, wherein a lock is provided to lock the test pipe in a selected orientation.

16. An apparatus for evaluating a liquid hydrocarbon to determine propensity for coke formation comprising:
 a chamber that has a first end and a second end;
 an injector arranged at the first end of the chamber;
 an air supply that supplies air to the injector at the first end of the chamber;
 a liquid hydrocarbon supply that supplies the liquid hydrocarbon to the injector at the first end of the chamber, the injector being arranged to atomise the liquid hydrocarbon and to supply the air and atomised liquid hydrocarbon into the chamber;
 a test pipe including an inlet and an outlet;
 a first connecting portion that directly connects the second end of the chamber to the test pipe;
 a second connecting portion that directly connects the second end of the chamber to the liquid hydrocarbon supply;
 a third connecting portion that connects the liquid hydrocarbon supply to the injector; and
 a heater that heats the test pipe,
 wherein the chamber is arranged to supply the atomised liquid hydrocarbon and air through the first connecting portion to the inlet of the test pipe, and the chamber supplies the liquid hydrocarbon through the second connecting portion to the liquid hydrocarbon supply, and
 the heater is arranged to heat the atomised liquid hydrocarbon and air as the atomised liquid hydrocarbon and air flow through the outlet of the test pipe.

17. An apparatus for evaluating a liquid hydrocarbon to determine propensity for coke formation comprising:
 a chamber that has a first end and a second end;
 an injector;
 an air supply that supplies air to the injector;
 a liquid hydrocarbon supply that supplies the liquid hydrocarbon to the injector, the injector being arranged at the first end of the chamber to atomise the liquid hydrocarbon and to supply the air and atomised liquid hydrocarbon into the chamber;
 a test pipe including an inlet and an outlet;
 a first connecting portion that connects the chamber to the test pipe and is arranged at the second end of the chamber;
 a second connecting portion that connects the chamber to the liquid hydrocarbon supply and is arranged at the second end of the chamber;
 a third connecting portion that connects the liquid hydrocarbon supply to the injector; and
 a heater that heats the test pipe, the heater being arranged around the test pipe only,
 wherein the chamber is arranged to supply the air and the atomised liquid hydrocarbon through the first connecting portion to the inlet of the test pipe, and supplies the liquid hydrocarbon through the second connecting portion to the liquid hydrocarbon supply, and
 the heater is arranged to heat the atomised liquid hydrocarbon and air only as the air and the atomised liquid hydrocarbon flow through the test pipe.

18. A method of evaluating a liquid hydrocarbon to determine propensity for coke formation, the method comprising:
 providing the apparatus of claim 1;
 supplying air to the injector;
 supplying the liquid hydrocarbon to the injector;
 atomising the liquid hydrocarbon;
 supplying air and atomised liquid hydrocarbon from the injector into the chamber;
 supplying the air and the atomised liquid hydrocarbon and air through the first connection portion to the test pipe;
 heating the test pipe to produce coking deposition in the test pipe; and
 measuring the mass of coking deposited in the test pipe.

19. The method as claimed in claim 18, comprising supplying lubricant or oil to the injector.

20. A method as claimed in claim 18, wherein the test pipe is variably mounted on a frame, the method further comprising varying the orientation of the test pipe relative to the frame and determining the propensity for coke formation at different orientations of the test pipe.

21. The method as claimed in claim 20, comprising arranging the test pipe at different angles relative to a vertical direction.

22. The method as claimed in claim 21, comprising arranging the test pipe at an angle of 45° relative to a vertical direction and arranging an outlet of the test pipe at a lesser height than an inlet of the test pipe.

23. The method as claimed in claim 21, comprising arranging the test pipe at an angle of 45° relative to a vertical direction and arranging an outlet of the test pipe at a greater height than an inlet of the test pipe.

24. The method as claimed in claim 21, comprising arranging the test pipe at an angle of 90° relative to a vertical direction and arranging an outlet of the test pipe at the same height as an inlet of the test pipe.

25. The method as claimed in claim 21, comprising arranging the test pipe parallel to a vertical direction and arranging an outlet of the test pipe at a greater height than an inlet of the test pipe.

26. The method as claimed in claim 20, comprising locking the test pipe in a selected orientation.

27. The method as claimed in claim 18, wherein the injector comprises:
- an inner cylindrical member;
- an outer cylindrical member that is coaxial with respect to the inner cylindrical member;
- an inner flow path that is formed within the inner cylindrical member;
- an outer annular flow path that is formed between the inner cylindrical member and the outer cylindrical member;
- the method further comprising supplying air to the inner flow path and supplying liquid hydrocarbon to the outer annular flow path.

28. The method according to claim 18, wherein the step of heating the test pipe heats the air and the atomised liquid hydrocarbon as the air and the atomised liquid hydrocarbon flow through the test pipe.

* * * * *